(12) United States Patent
Grunden et al.

(10) Patent No.: US 11,690,612 B2
(45) Date of Patent: Jul. 4, 2023

(54) SELF-LOCKING SURGICAL CONSTRUCTS AND METHODS OF USE

(71) Applicant: Arthrex, Inc., Naples, FL (US)

(72) Inventors: Daniel T. Grunden, Naples, FL (US); Samuel Bachmaier, Mauern (DE)

(73) Assignee: Arthrex, Inc., Naples, FL (US)

( * ) Notice: Subject to any disclaimer, the term of this patent is extended or adjusted under 35 U.S.C. 154(b) by 128 days.

(21) Appl. No.: 17/133,950

(22) Filed: Dec. 24, 2020

(65) Prior Publication Data

US 2021/0186488 A1  Jun. 24, 2021

Related U.S. Application Data

(60) Provisional application No. 62/953,448, filed on Dec. 24, 2019, provisional application No. 62/968,309, filed on Jan. 31, 2020, provisional application No. 62/958,767, filed on Jan. 9, 2020.

(51) Int. Cl.
*A61B 17/04* (2006.01)
*A61F 2/08* (2006.01)

(52) U.S. Cl.
CPC ........ *A61B 17/0487* (2013.01); *A61F 2/0811* (2013.01); *A61B 2017/0404* (2013.01); *A61F 2002/0852* (2013.01); *A61F 2002/0882* (2013.01)

(58) Field of Classification Search
CPC ............ A61B 17/0487; A61B 17/0401; A61B 17/06166; A61B 2017/0404; A61F 2/0811; A61F 2002/0852; A61F 2002/0882; A61F 2250/0004
See application file for complete search history.

(56) References Cited

U.S. PATENT DOCUMENTS

| | | |
|---|---|---|
| 5,306,301 A | 4/1994 | Graf et al. |
| 7,481,825 B2 | 1/2009 | Bonutti |
| 8,672,968 B2 | 3/2014 | Stone et al. |
| 8,724,491 B2 | 5/2014 | Kim et al. |
| 8,865,797 B2 | 10/2014 | Matyjaszewski et al. |
| 8,926,661 B2 | 1/2015 | Sikora et al. |
| 9,486,211 B2 | 11/2016 | Stone et al. |
| 9,498,204 B2 | 11/2016 | Denham et al. |
| 9,572,655 B2 | 2/2017 | Denham et al. |
| 9,636,102 B2 | 5/2017 | Sikora et al. |
| 9,642,610 B2 | 5/2017 | Albertorio et al. |
| 9,687,338 B2 | 6/2017 | Albertorio et al. |
| 9,801,625 B2 | 10/2017 | Dooney, Jr. et al. |
| 9,801,708 B2 | 10/2017 | Denham et al. |
| 9,833,230 B2 | 12/2017 | Stone |
| 9,918,711 B2 | 3/2018 | Seavey |
| 10,004,493 B2 | 6/2018 | Stone et al. |
| 10,092,288 B2 | 10/2018 | Denham et al. |
| 10,194,900 B2 | 2/2019 | Ferguson et al. |
| 10,238,484 B2 | 3/2019 | Albertorio et al. |
| 10,245,016 B2 | 4/2019 | Zajac et al. |
| 10,251,686 B2 | 4/2019 | Zajac et al. |
| 10,285,801 B2 | 5/2019 | Roller et al. |
| 10,299,784 B2 | 5/2019 | Anderson |

(Continued)

*Primary Examiner* — Phong Son H Dang

(74) *Attorney, Agent, or Firm* — Blank Rome LLP

(57) ABSTRACT

Surgical constructs that at least one fixation device, at least one flexible strand the forms at least one adjustable loop, and a self-locking mechanism, and methods of tissue repair using the same.

13 Claims, 8 Drawing Sheets

(56) References Cited

U.S. PATENT DOCUMENTS

| | | |
|---|---|---|
| 10,349,931 B2 | 7/2019 | Stone |
| 10,398,428 B2 | 9/2019 | Denham et al. |
| 10,405,848 B2 | 9/2019 | Sikora et al. |
| 10,646,216 B2 | 5/2020 | Paterson et al. |
| 10,646,327 B2 | 5/2020 | Lund |
| 10,660,682 B2 | 5/2020 | Vitale et al. |
| 10,864,028 B2 | 12/2020 | Zajac et al. |
| 2001/0041938 A1 | 11/2001 | Hein |
| 2012/0095470 A1* | 4/2012 | Kaiser ................ A61B 17/1675 606/80 |
| 2018/0249998 A1 | 9/2018 | Chavan et al. |
| 2019/0038276 A1* | 2/2019 | Jackson ................ A61F 2/0811 |
| 2019/0105029 A1 | 4/2019 | Ferguson et al. |
| 2019/0125333 A1 | 5/2019 | Moore |
| 2019/0321026 A1 | 10/2019 | Sikora et al. |
| 2019/0328382 A1* | 10/2019 | Stone ................ A61B 17/0482 |
| 2020/0015804 A1* | 1/2020 | Bachmaier ............ A61F 2/0811 |
| 2020/0022730 A1 | 1/2020 | Manitzaris et al. |
| 2020/0093514 A1 | 3/2020 | Perez et al. |
| 2020/0138562 A1* | 5/2020 | Hernandez ............ A61F 2/0811 |
| 2020/0170634 A1* | 6/2020 | Burkhart ................ A61F 2/0811 |
| 2020/0360009 A1* | 11/2020 | Lombardo ......... A61B 17/0401 |
| 2021/0000465 A1* | 1/2021 | Kam .................. B65D 73/0078 |
| 2021/0093316 A1* | 4/2021 | Gustafson ......... A61B 17/0485 |
| 2021/0128138 A1* | 5/2021 | Bettenga ............ A61F 2/0811 |
| 2021/0378654 A1* | 12/2021 | Lombardo ....... A61B 17/06066 |
| 2022/0265261 A1* | 8/2022 | Hernandez ......... A61B 17/0401 |

\* cited by examiner

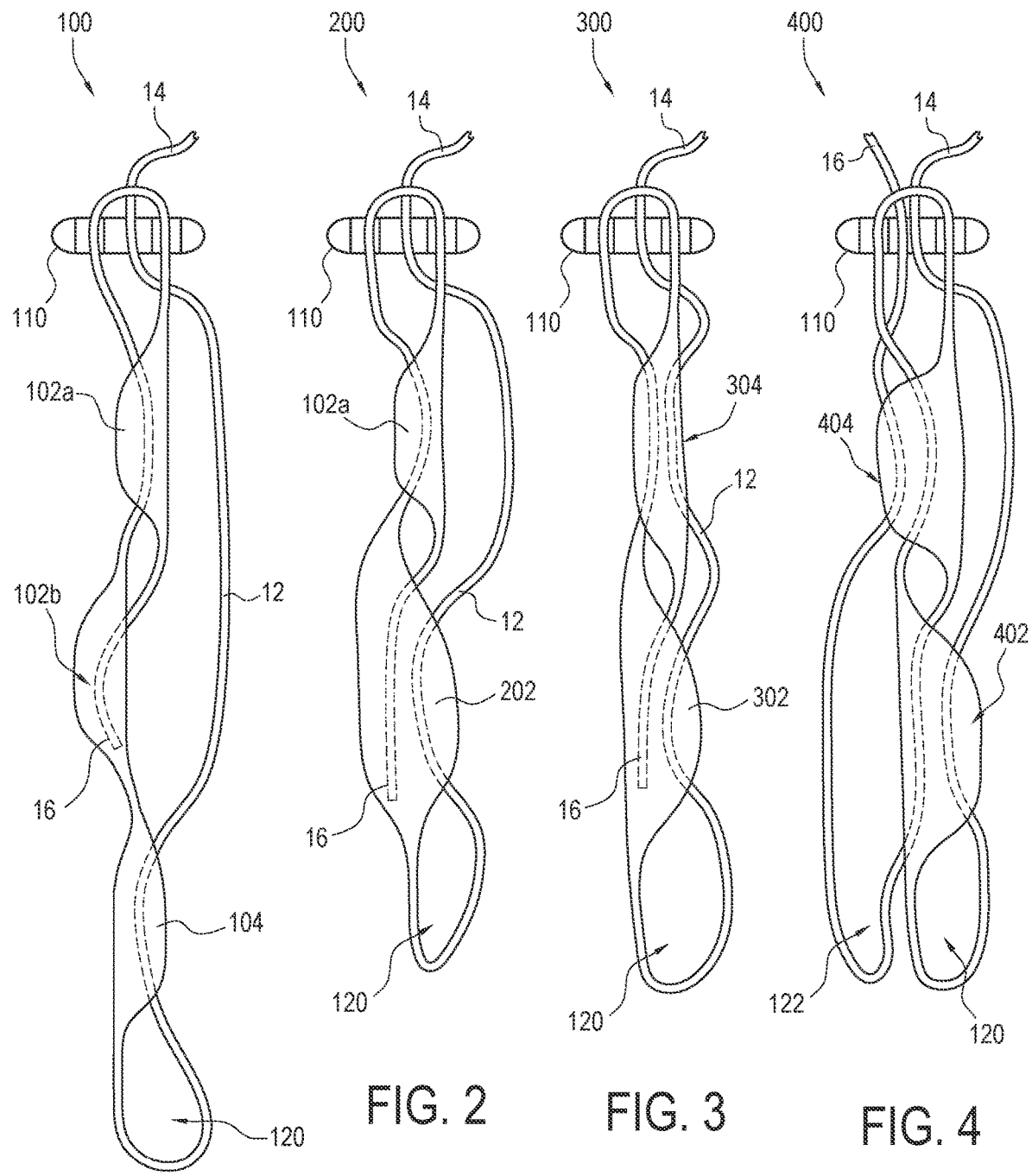

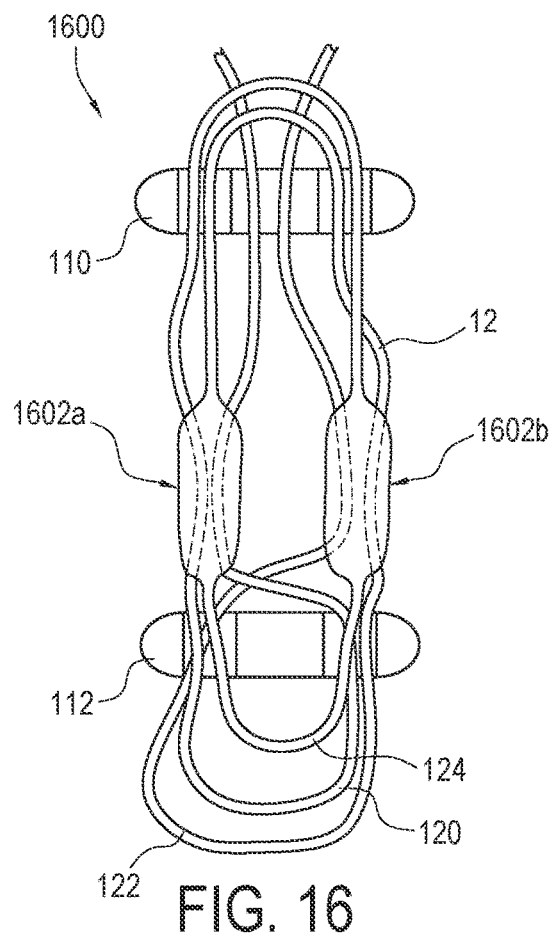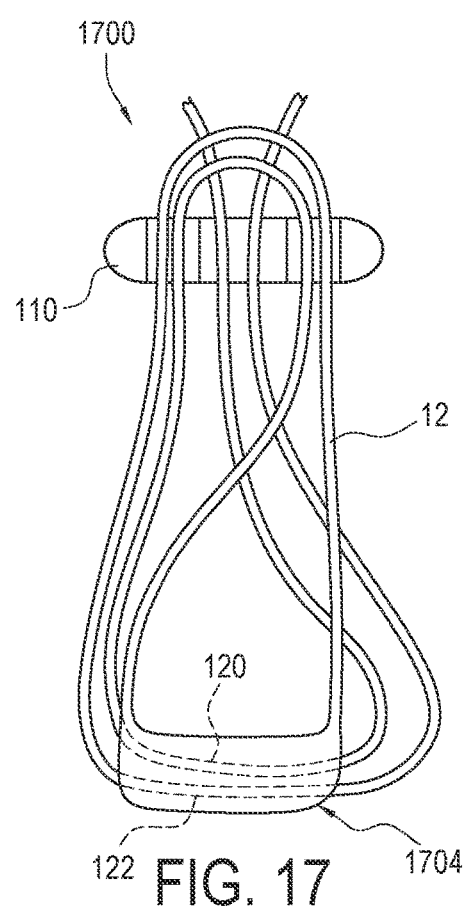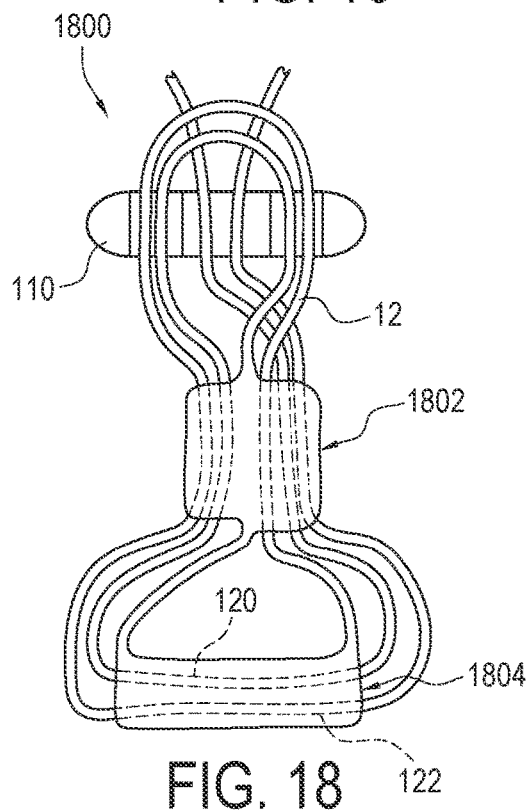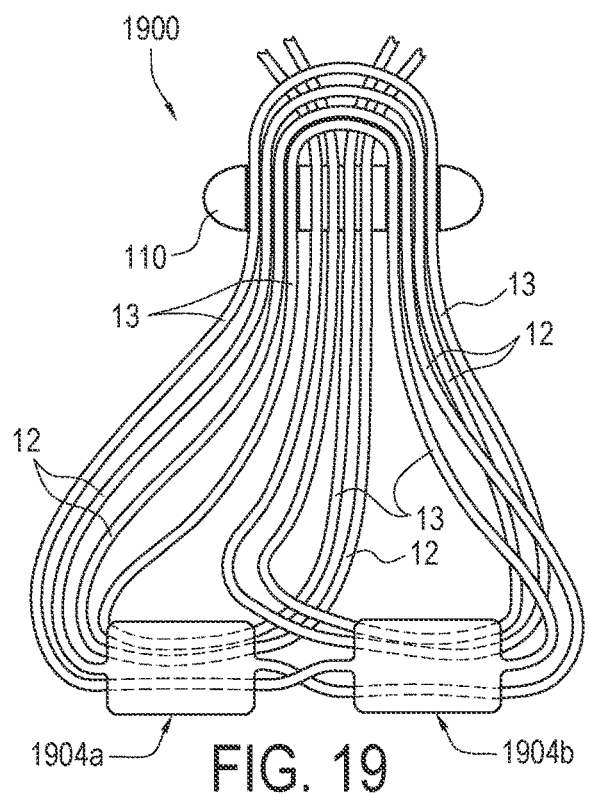

SELF-LOCKING SURGICAL CONSTRUCTS AND METHODS OF USE

CROSS-REFERENCE TO RELATED APPLICATIONS

This application claims priority to U.S. Provisional Application Ser. No. 62/953,448, filed on Dec. 24, 2019, U.S. Provisional Application Ser. No. 62/958,767, filed on Jan. 8, 2020, and U.S. Provisional Application Ser. No. 62/968,309 filed on Jan. 31, 2020, each of which is relied upon and incorporated herein by reference in its entirety.

BACKGROUND

This disclosure relates to surgical reconstruction, such as for joint or ligament repair, and associated surgical constructs. Tissue reconstruction surgeries, such as anterior cruciate ligament (ACL) reconstructions and posterior cruciate ligament (PCL) reconstructions, typically involve drilling a tunnel through bone, positioning a substitute graft into the bone tunnel, and fixating the graft within the bone tunnel using a fixation device, such as a button, a screw, or the like.

SUMMARY

This disclosure provides techniques and reconstruction systems for fixation of soft tissue to bone or bone to bone. The reconstruction system of the disclosure may comprise a surgical construct with at least one fixation device, such as a button, and at least one flexible strand with at least one adjustable loop coupled to the fixation device and connectable to tissue (such as soft tissue, graft, tendon, ligament, synthetic material, biological material, bone, or combinations of such materials, among others), wherein the construct is self-locking with one or more self-locking splices or one or more finger trap mechanisms, or a combination of both. The tissue may be directly looped over the flexible, adjustable loop for insertion and fixation into a bone tunnel or socket.

This disclosure may provide, for example, a surgical construct that comprises at least one fixation device; at least one flexible strand that forms at least one adjustable loop, the adjustable loop being coupled to the at least one fixation device; and a self-locking mechanism that includes one or more self-locking splices, one or more finger trap mechanisms, or a combination of one or more self-locking splices and one or more finger trap mechanisms.

In some aspects of this disclosure, the construct further comprises another fixation device coupled to the at least one adjustable loop; each fixation device is a button; and/or at least one of the buttons is coupled to the adjustable loop remote from the self-locking mechanism.

In other aspects, the flexible strand forms at least two adjustable loops; the at least two adjustable loops are interlocked with one another; the at least one flexible strand is a single strand; the self-locking mechanism is one of the self-locking splices merged with one of the finger trap mechanisms; the self-locking mechanism is one of the finger trap mechanisms and receives two adjustable loops of the flexible strand; the self-locking mechanism is first and second finger trap mechanisms that each receive an adjustable loop of the flexible strand; the construct further comprises one or more splices that receives one or more segments of the flexible strand for strand management of the construct; and/or the construct further comprises another flexible strand forming at least one adjustable loop coupled to the at least one fixation device.

The disclosure may also provide, for example, a surgical construct that comprises at least one fixation device; at least one flexible strand that forms at least two adjustable loops, each adjustable loop being coupled to the at least one fixation device; and a self-locking mechanism including one or more self-locking splices, one or more finger trap mechanisms, or a combination of one or more self-locking splices and one or more finger trap mechanisms. And the self-locking mechanism receives portions of the at least two adjustable loops.

In some aspects of this disclosure, the at least one fixation device is a button and is coupled to the at least two adjustable loops remote from the self-locking mechanism; the construct further comprises another fixation device coupled to the at least two adjustable loops; and/or the at least one flexible strand is a single strand.

This disclosure may further provide a method of tissue repair using a surgical construct that comprises at least one fixation device, at least one flexible strand that forms at least one adjustable loop coupled to the fixation device, and a self-locking mechanism. The method may comprise the steps of: drilling a bone tunnel; looping tissue over the at least one adjustable loop of the construct; advancing the surgical construct with the looped tissue through the bone tunnel; securing the tissue within the bone tunnel by adjusting the length of the adjustable loop; and locking the construct in place via the self-locking mechanism of the construct.

In certain aspects of this disclosure, the method further comprises the step of coupling another fixation device to the at least one adjustable loop; the surgical construct forms at least two adjustable loops each coupled to the at least one fixation device, and the length of each of the at least two adjustable loops is adjusted when securing the tissue; and/or the self-locking mechanism receives portions of each of the at least two adjustable loops.

This summary is not intended to identify essential features of the claimed subject matter, nor is it intended for use in determining the scope of the claimed subject matter. It is to be understood that both the foregoing general description and the following detailed description are exemplary and are intended to provide an overview or framework to understand the nature and character of the disclosure.

BRIEF DESCRIPTION OF THE DRAWINGS

The accompanying drawings are incorporated in and constitute a part of this specification. It is to be understood that the drawings illustrate only some examples of the disclosure and other examples or combinations of various examples that are not specifically illustrated in the figures may still fall within the scope of this disclosure. Examples will now be described with additional detail through the use of the drawings, in which:

FIGS. 1-21 show exemplary embodiments of this disclosure.

DETAILED DESCRIPTION

Figure 5:
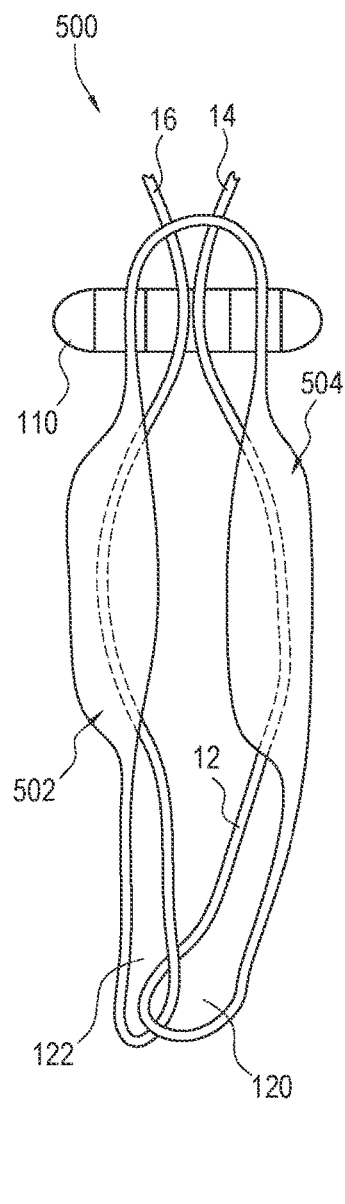

This disclosure generally relates to self-locking surgical constructs and methods of tissue reconstruction using the same. The surgical constructs are designed to simplify reconstructive surgery while also providing a secure repair. The surgical constructs of the disclosure may be used to perform a variety of tissue reconstruction procedures. The tissue reconstruction procedures could include any procedure in which it is desirable to position a replacement graft or filament within a bone tunnel to repair torn tissue. ACL and PCL reconstructions are but two non-limiting examples of reconstruction procedures which could benefit from the use of the surgical fixation system of this disclosure.

In a first exemplary embodiment of the disclosure, a surgical construct 100 generally includes a fixation device 110 and a flexible adjustable loop 120 connected to the fixation device 110, as seen in FIG. 1. The loop 120 can carry, for example, a graft for fixating the graft relative to bone and/or a filament (e.g., suture, etc.) for fixating the filament relative to bone.

Loop 120 may be an adjustable loop made of a flexible material and/or one or more strands 12, such as suture, suture tape, or the like, and includes an adjustable length and perimeter. One or more of the opposite free ends 14 and 16 of the strand 12, which may also be referred to as shortening strands, may be pulled to reduce the size of the loop 120. For example, the loop 120 may be adjusted in a first direction by pulling on the strand's free end 14 but is prevented from loosening in the opposite direction due to applied internal tensile forces. For coupling to loop 120, fixation device 110 may have two openings, for example, similar to the button disclosed in commonly owned U.S. Pat. No. 8,460,379, the subject matter of which is herein incorporated by reference.

Surgical construct 100 may be provided with one or more self-locking splices, one or more self-locking finger trap mechanisms, or a combination of any number of self-locking splices with any number of finger trap mechanisms. As seen in FIG. 1, for example, construct 100 may have first and second self-locking splices 102a and 102b and a single finger trap 104 formed in the flexible strand 12 of the loop. The self-locking splices 102a and 102b are formed by splicing the flexible material or strand 12 that is used to form the loop 120 through itself. The splice may be formed, for example, by two spaced apertures in a length of the strand 12 with a tunnel therein connecting the two apertures. The loop 120 may be connected to the fixation device 110 prior to completely forming the loop 120. Free end 14 of strand 12 may be threaded through finger trap 104 to form loop 120 and then through the button 110 for tensioning the loop. Once strand 12 is threaded through the openings of button 110, the strand's other free end 16 may be threaded through the two self-locking splices 102a and 102b to lock the repair. In an alternative embodiment, two of the constructs 100 may be wrapped around the button 110 in parallel.

As seen in FIG. 2, in a second exemplary embodiment of the disclosure, a surgical construct 200 is similar to construct 100, except that the second self-locking splice 102b and finger trap mechanism 104 (FIG. 1) are merged into one self-locking mechanism 202. As such, both the strand 12 and its free end 16 thread through the merged self-locking mechanism 202.

As seen in FIG. 3, in a third exemplary embodiment of the disclosure, a surgical construct 300 is similar to the construct 200 of the second embodiment in that it includes a merged self-locking mechanism 302 (like mechanism 202) with a second merged self-locking mechanism 304 that merges the first self-locking splice 102a of the first embodiment with a second finger trap mechanism. As such, the strand 12 forming the loop 120 threads through second merged self-locking mechanism 304.

As seen in FIG. 4, a fourth embodiment of the disclosure includes a surgical construct 400 that is similar to the construct 300 of the third embodiment with a second loop 122 added. As such, both free ends 14 and 16 of the strand 12 forming the loops 120 and 122 extend through the button 110 for tensioning the loops. Construct 400 may have first and second merged self-locking mechanisms 402 and 404 like the mechanisms 302 and 304 of construct 300.

A surgical construct 500 according to a fifth exemplary embodiment of the disclosure may also include first and second loops 120 and 122, similar to the construct 400 of the fourth embodiment, where the loops 120 and 122 are interlocked, as seen in FIG. 5. Construct 500 may include first and second finger trap mechanisms 502 and 504 to form the loops which forms a 4-strand segment repair. The self-locking splices of the fourth embodiment are not required for construct 500.

Figure 6:
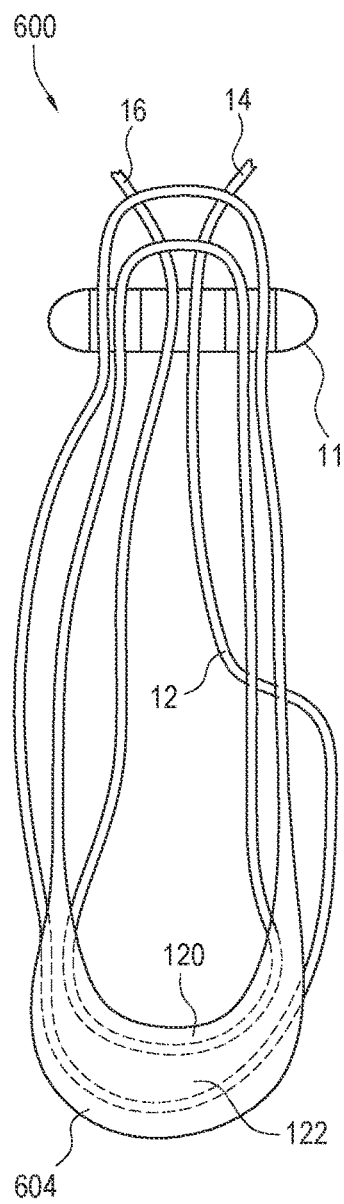

As seen in FIG. 6, in a sixth exemplary embodiment of the disclosure, a surgical construct 600, the loops may be threaded through the button 110 twice and threaded through a single finger trap mechanism 604 to form a 6-strand segment repair. In this embodiment, the loops may be separate and not interlocked.

Figure 7:
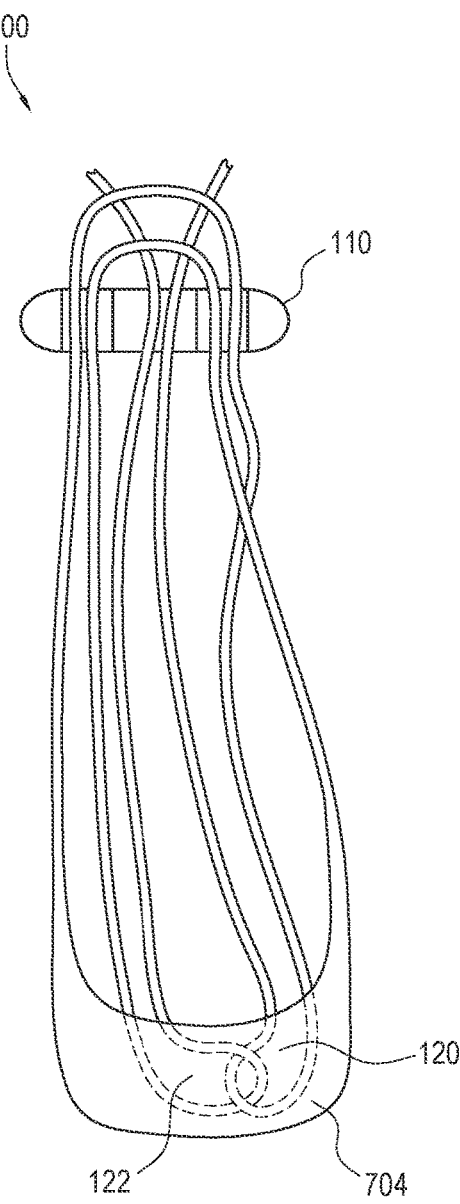

As seen in FIG. 7, in a seventh exemplary embodiment of the disclosure, a surgical construct 700 is similar to construct 600 of the sixth embodiment, except the loops 120 and 122 are interlocked. Like construct 600, construct 700 may have a single finger trap mechanism 704 and the interlocked portion of the interlocked loops 120 and 122 may be received in the finger trap mechanism 704. The second strand segment of the construct 700 goes into and out of the same aperture of the finger trap mechanism 704 as the first strand segment and the third strand segment of the construct 700 also goes into and out of the same aperture as the first strand segment.

Figure 8:
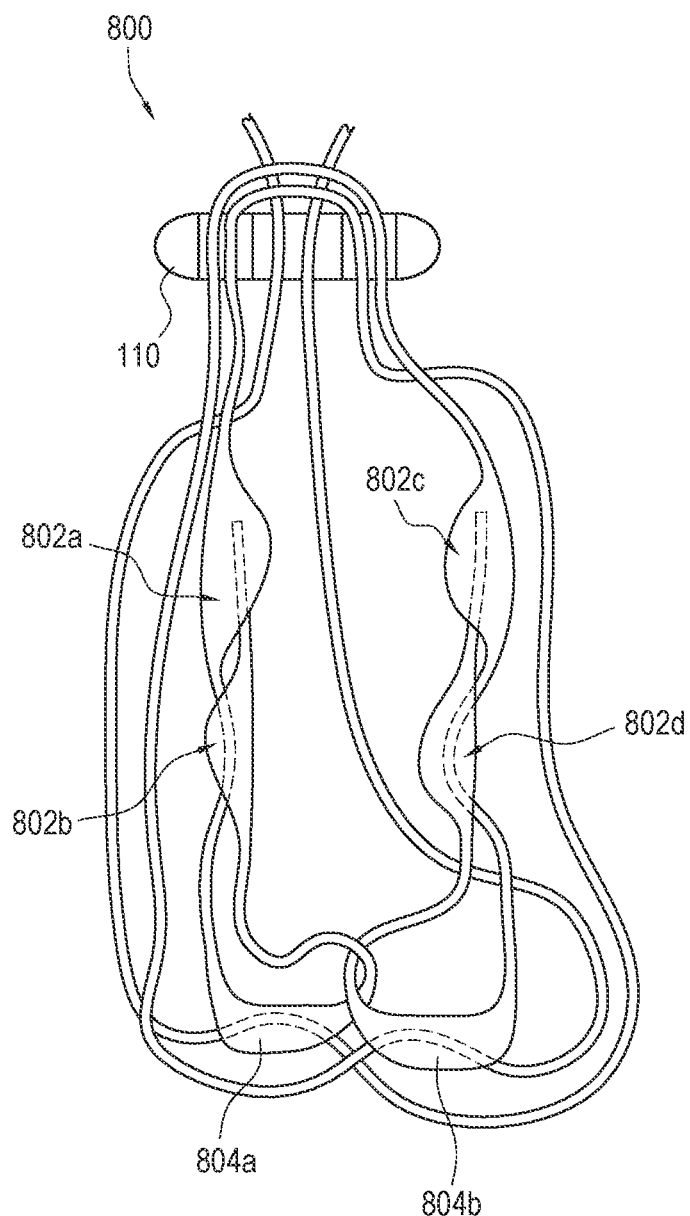

As seen in FIG. 8, a surgical construct 800 according to an eight exemplary embodiment of the disclosure may include multiple strands, multiple loops with multiple self-locking splices 802a, 802b, 802c, and 802d and multiple finger trap mechanisms 804a and 804b.

Figure 9:
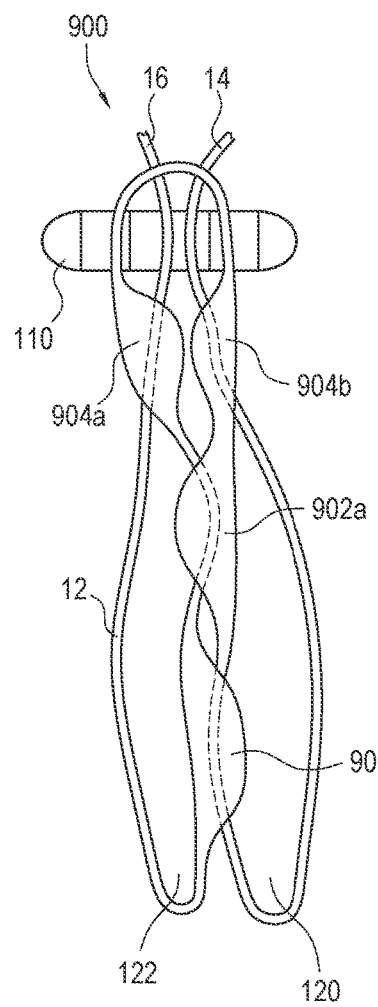

As seen in FIG. 9, a surgical construct 900 according to a ninth exemplary embodiment of the disclosure may be similar to construct 400 of the fourth embodiment, except that the merged self-locking mechanisms 402 and 404 of construct 400 are split. That is first and second self-locking splices 902a and 902b are provided to interlock the loops 120 and 122 of construct 900 and first and second finger trap mechanisms 904a and 904b are provided near the button 110.

Figure 10:
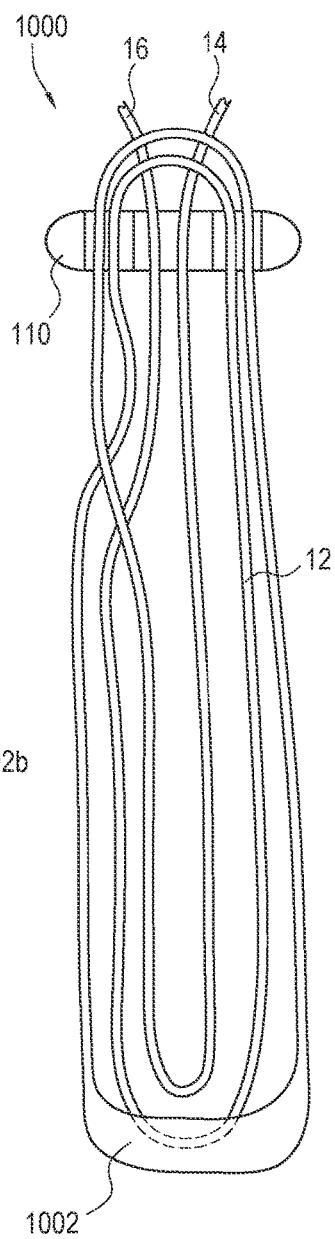

As seen in FIG. 10, in a tenth exemplary embodiment of the disclosure, a surgical construct 1000 is similar to construct 600 of the sixth embodiment, except that construct 1000 has only a single self-locking splice 1002.

Figure 11:
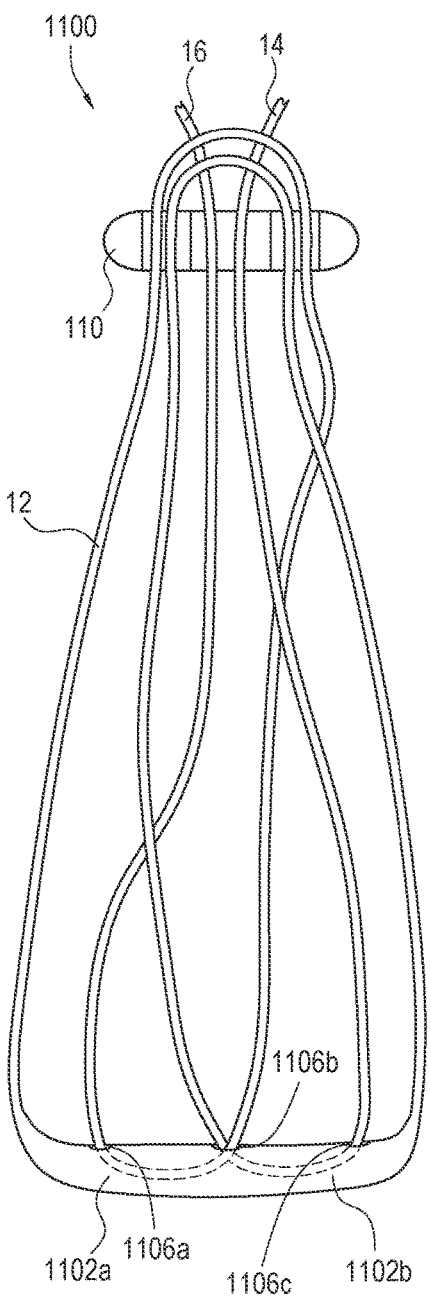

As seen in FIG. 11, in an eleventh exemplary embodiment of the disclosure, a surgical construct 1100 is similar to construct 600 of the sixth embodiment, except that there are two splices 1102a and 1102b next to each other and formed such that only three apertures 1106a, 1106b, and 1106c for accessing the splices are needed and provided.

Figure 12:
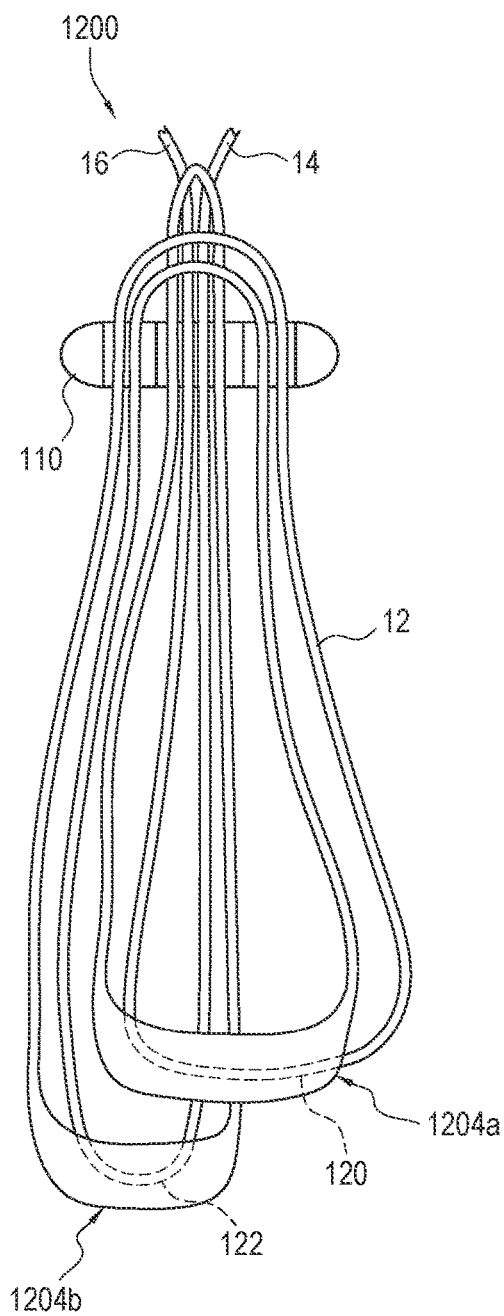

As seen in FIG. 12, in a twelfth exemplary embodiment of the disclosure, a surgical construct 1200 is similar to construct 600 of the sixth embodiment, except that there are two separate finger trap mechanism 1204a and 1204b (instead of a single finger trap mechanism). Each finger trap mechanism 1204a and 1204b may receive one of the strand loops 120 and 122.

Figure 13:
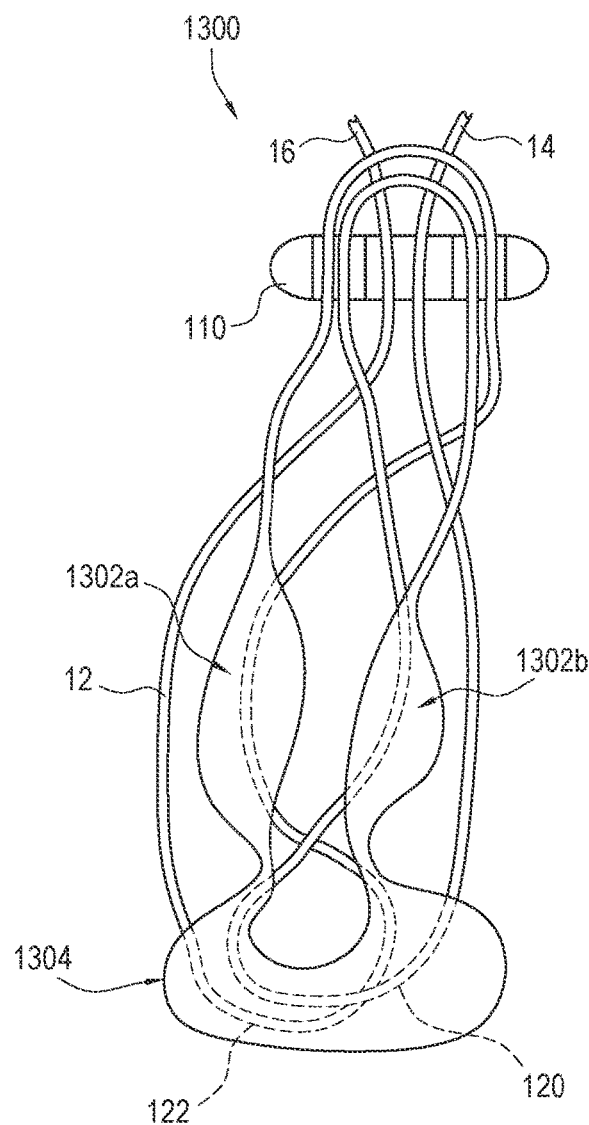
Figure 14:
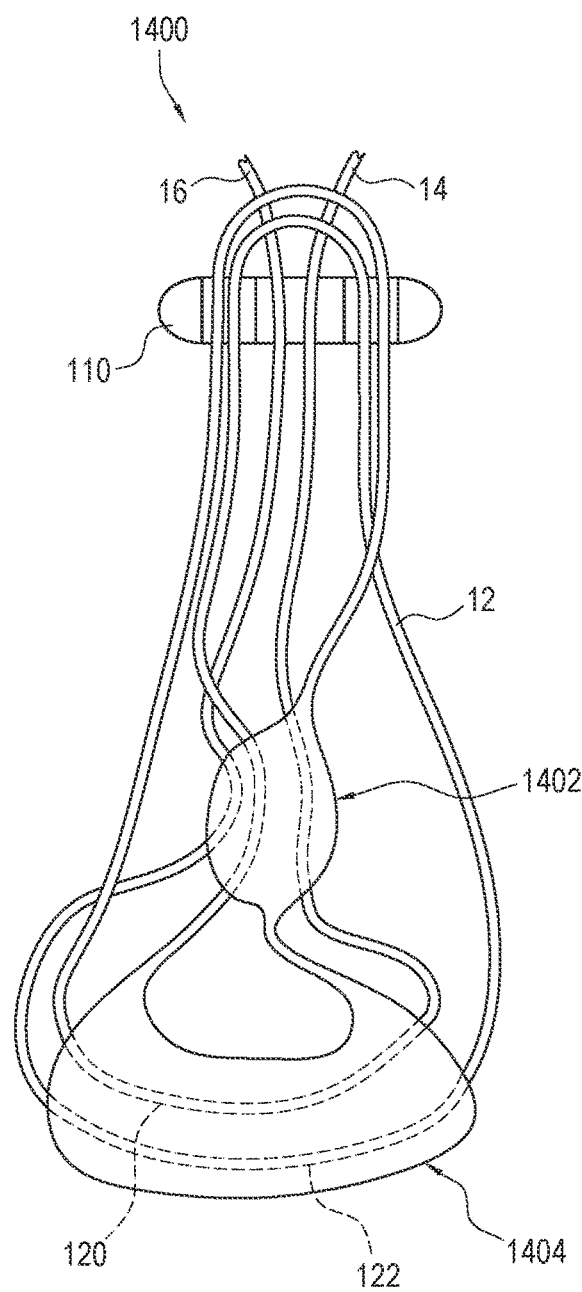

FIGS. 13 and 14 illustrate thirteenth and fourteenth exemplary embodiments, respectively, of the disclosure, which are both similar to the sixth embodiment. As seen in FIG. 13, a surgical construct 1300 is similar to construct 600 of the sixth embodiment and includes first and second self-locking splices 1302*a* and 1302*b* in addition to a single finger trap mechanism 1304 (that receives both strand loops 120 and 122), where each splice 1302*a* and 1302*b* receives a strand segment of the construct for strand management thereof. Similarly, as seen in FIG. 14, a surgical construct 1400 includes a single self-locking mechanism 1402 in addition to a single finger trap mechanism 1404 (which receives both strand loops 120 and 122), where the single self-locking mechanism 1402 receives multiple strand segments for strand management of the construct.

Figure 15:
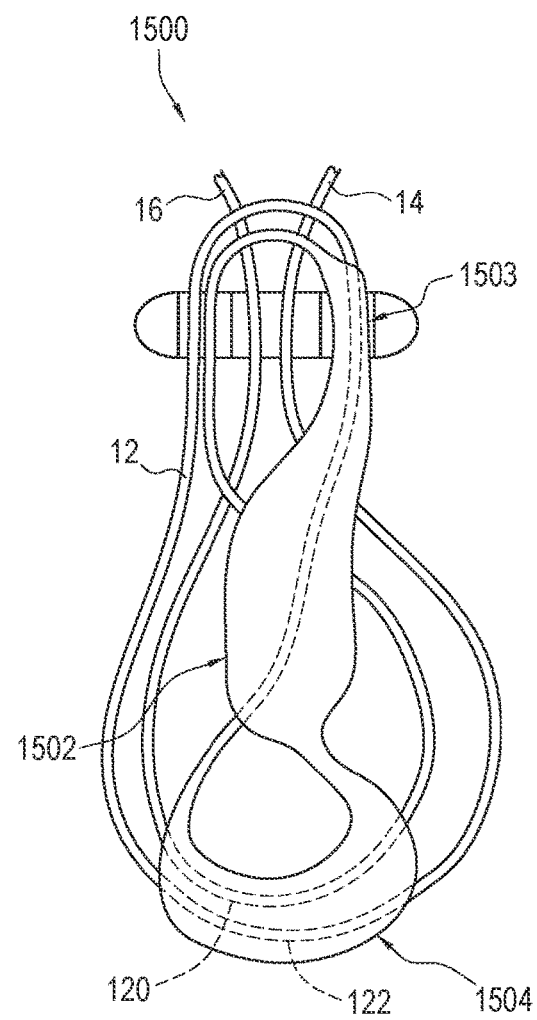

As seen in FIG. 15, in a fifteenth exemplary embodiment of the disclosure, a surgical construct 1500 is similar to construct 600 of the sixth embodiment and includes a self-locking splice 1502 in addition to a finger trap mechanism 1504 (which receives both of the strand loops 120 and 122). The self-locking splice 1502 may receive a strand segment and may have an elongated portion 1503 that is configured to extend through one of the apertures of the button 110 for strand management of the construct.

As seen in FIG. 16, in a sixteenth exemplary embodiment of the disclosure, a surgical construct 1600 is similar to construct 1300 of the thirteenth embodiment, except that construct 1600 does not include a finger trap mechanism. Instead, the construct 1600 has a third strand loop 124 extending between first and second self-locking splices 1602*a* and 1602*b* and a second fixation device 112. The second fixation device 112 can be located on the other side of self-locking splices 1602*a* and 1602*b* from fixation device 110. Two segments of the strand 12 thread through each of the self-locking splices 1602*a* and 1602*b*. The second fixation device 112 is coupled to each of the strand loops 120, 122, and 124.

As seen in FIG. 17, in a seventeenth exemplary embodiment of the disclosure, a surgical construct 1700 is similar to construct 600 of the sixth embodiment including having a finger trap mechanism 1704 through which the strand loops 120 and 122 may be threaded. The direction of the loops 120 and 122 are different than in construct 600. In construct 1700, at least one strand segment of the loops 120 and 122 cross over two other strand segments.

As seen in FIG. 18, in an eighteenth exemplary embodiment of the disclosure, a surgical construct 1800 is similar to construct 1500 of the fifteenth embodiment, except all of the strand segments converge and splice into one. Like construct 1500, construct 1800 includes a self-locking splice 1802 in addition to a finger trap mechanism 1804 (which receives both of the strand loops 120 and 122). The self-locking splice 1802 receives each strand segment.

As seen in FIG. 19, in a nineteenth exemplary embodiment of the disclosure, a surgical construct 1900 is similar to construct 600 of the sixth embodiment, except construct 1900 has twice as many tensioning strands, strands 12 and 13. Two finger trap mechanisms 1904*a* and 1904*b* are provided in this construct to capture and organize the loops of each strand 12 and 13.

Figure 20:
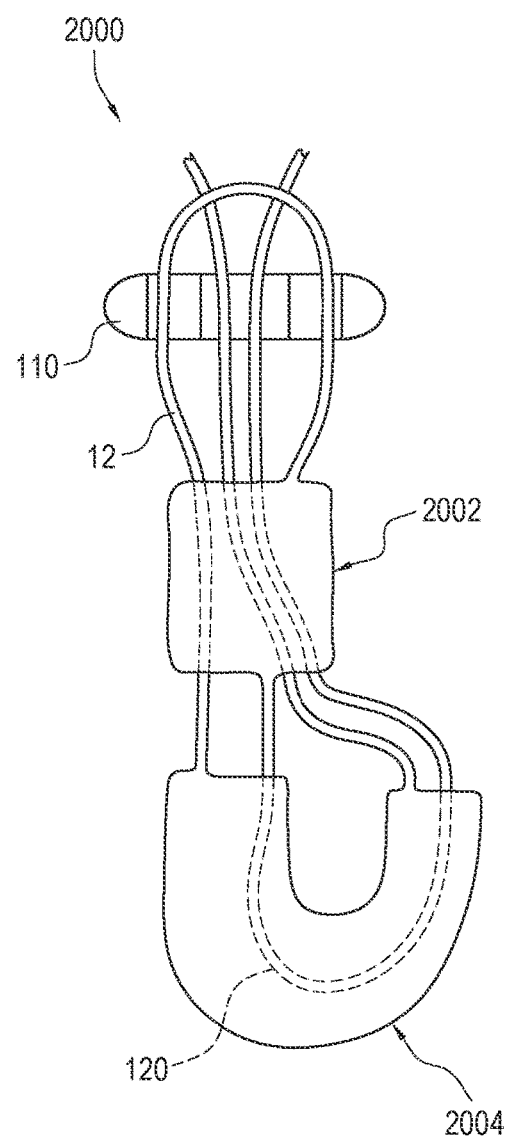

As seen in FIG. 20, in a twentieth exemplary embodiment of the disclosure, a surgical construct 2000 is similar to construct 1500 of the fifteenth embodiment, except the strand has one loop 120. Like construct 1500, construct 2000 includes a self-locking splice 2002 a finger trap mechanism 2004. The self-locking splice 2002 receives each segment of the strand 12 and the finger trap mechanism 2004 receives the strand loop 120. Finger trap mechanism 2004 may be elongated to facilitate loading of the fixation device. 110.

Figure 21:
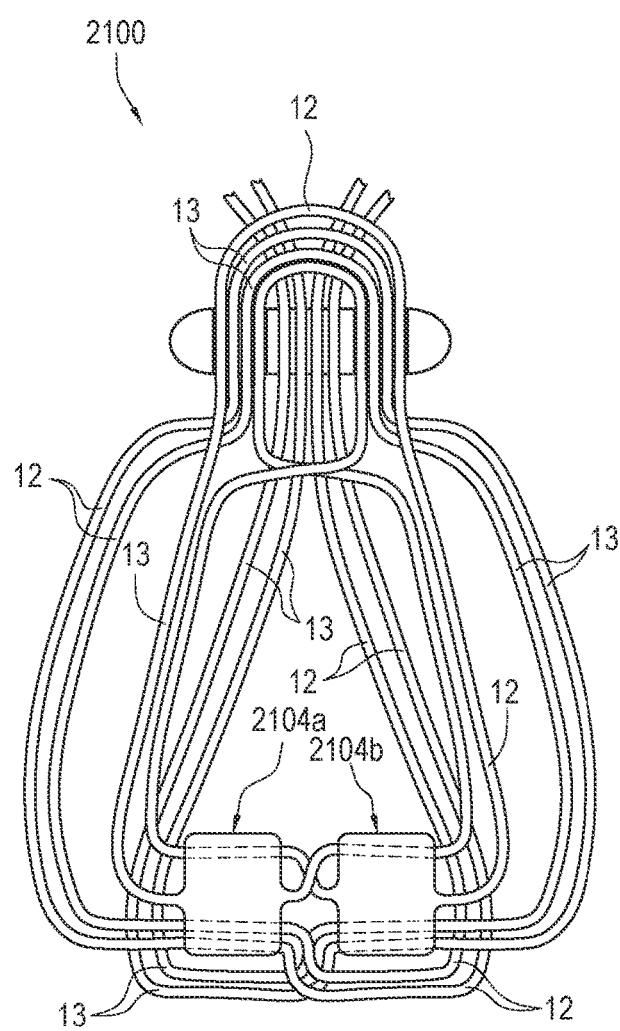

As seen in FIG. 21, in a twenty-first exemplary embodiment of the disclosure, a surgical construct 2100 is similar to construct 1900 of the nineteenth embodiment, except that the first strand 12 does not splice back into itself and the second strand 13 does not splice back into itself, leaving strand loops thereof outside of finger trap mechanisms 2104*a* and 2104*b*.

In an embodiment, each of the fixation devices 110 and 112 can be a button. However, fixation devices having other similar configurations could also be used. The fixation device 110 may be oblong or round and may be made of either metallic or polymeric materials within the scope of this disclosure.

The disclosure may also provide methods of fixation of bone to bone, or soft tissue to bone. An exemplary method of the present invention comprises the steps of: (i) providing a bone tunnel; (ii) providing a button/graft construct, such as the surgical constructs of the embodiments discussed above, in the vicinity of the bone tunnel; (iii) looping tissue (graft) over the adjustable loop of the construct; (iv) advancing the button/graft construct with the looped tissue through the bone tunnel; and (v) securing the tissue within the bone tunnel by adjusting the length of the adjustable loop and locking the construct in place via the self-locking splices and/or the finger trap mechanisms of the construct.

It should be understood that terms such as "lateral," "medial," "distal," "proximal," "superior," and "inferior" are used above consistent with the way those terms are used in the art. Further, these terms have been used herein for purposes of explanation and should not be considered otherwise limiting. Terms such as "generally," "substantially," and "about" are not intended to be boundary less terms and should be interpreted consistent with the way one skilled in the art would interpret those terms.

Although the different examples have the specific components shown in the illustrations, embodiments of this disclosure are not limited to those particular combinations. It is possible to use some of the components or features from one of the examples in combination with features or components from another one of the examples.

One of ordinary skill in this art would understand that the above-described embodiments are exemplary and non-limiting. That is, modifications of this disclosure would come within the scope of the claims. Accordingly, the following claims should be studied to determine their true scope and content.

What is claimed is:

1. A surgical construct, comprising: at least one fixation device; at least one flexible strand that forms at least two adjustable loops on a side of the at least one fixation device, the at least two adjustable loops being interlocked with one another on the side of the at least one fixation device; and a self-locking mechanism including one or more self-locking splices, one or more finger trap mechanism, or a combination of one or more self-locking splice and one or more finger trap mechanism on the same side of the at least one fixation device as the at least two adjustable loops.

2. The construct of claim 1, further comprising another fixation device coupled to the at least two adjustable loops.

3. The construct of claim 2, wherein each fixation device is a button.

4. The construct of claim 3, wherein at least one of the buttons is coupled to the adjustable loop remote from the self-locking mechanism.

5. The construct of claim 1, wherein the at least one flexible strand is a single strand.

6. The construct of claim 1, further comprising one or more splices that receives one or more segments of the flexible strand for strand management of the construct.

7. A surgical construct, comprising:
- at least one fixation device;
- at least one flexible strand that forms at least one adjustable loop, the adjustable loop being coupled to the at least one fixation device; and
- a self-locking mechanism including one or more self-locking splices, one or more finger trap mechanisms, or a combination of one or more self-locking splices and one or more finger trap mechanisms, wherein the self-locking mechanism comprises one of the self-locking splices merged with one of the finger trap mechanisms.

8. The construct of claim 7, wherein the flexible strand forms at least two adjustable loops, and the at least two adjustable loops are interlocked with one another.

9. A surgical construct, comprising:
- at least one fixation device;
- at least one flexible strand that forms at least one two adjustable loops, the at least two adjustable loops being coupled to the at least one fixation device; and
- a self-locking mechanism including one or more self-locking splices, one or more finger trap mechanisms, or a combination of one or more self-locking splices and one or more finger trap mechanisms, wherein the self-locking mechanism comprises one of the finger trap mechanisms and receives the two adjustable loops of the flexible strand.

10. A surgical construct, comprising:
- at least one fixation device;
- at least one flexible strand that forms at least one adjustable loop, the adjustable loop being coupled to the at least one fixation device; and
- a self-locking mechanism including one or more self-locking splices, one or more finger trap mechanisms, or a combination of one or more self-locking splices and one or more finger trap mechanisms, wherein the self-locking mechanism comprises first and second finger trap mechanisms that each receive an adjustable loop of the flexible strand.

11. The construct of claim 10, wherein the flexible strand forms at least two adjustable loops.

12. A surgical construct, comprising:
- at least one fixation device for fixing tissue to bone;
- at least two flexible strands, each of the at least two flexible strands forming at least one adjustable loop, the adjustable loop formed by each of the flexible strands being coupled to the at least one fixation device; and
- a self-locking mechanism including one or more self-locking splices, one or more finger trap mechanisms, or a combination of one or more self-locking splices and one or more finger trap mechanisms.

13. Method of tissue repair using the surgical construct of claim 1, the method comprising the steps of:
- drilling a bone tunnel;
- looping tissue over the at least two adjustable loops of the surgical construct;
- advancing the surgical construct with the looped tissue through the bone tunnel;
- securing the tissue within the bone tunnel by adjusting the length of the adjustable loops; and
- locking the surgical construct in place via the self-locking mechanism of the construct.

* * * * *